United States Patent

Kanesaki et al.

Patent Number: 5,484,872
Date of Patent: Jan. 16, 1996

[54] CYCLIC SULFIDE COMPOUND, POLYMERIZABLE COMPOSITIONS FOR OPTICAL PRODUCTS AND OPTICAL PRODUCTS FORMED THEREOF

[75] Inventors: Hiroyuki Kanesaki, Amagasaki; Tetsuyuki Saika, Suita; Masafumi Mikami, Kurume, all of Japan

[73] Assignee: Daiso Co., Ltd., Osaka, Japan

[21] Appl. No.: 403,648

[22] Filed: Mar. 14, 1995

Related U.S. Application Data

[62] Division of Ser. No. 35,598, Mar. 23, 1993, Pat. No. 5,446,173.

[30] Foreign Application Priority Data

Mar. 24, 1992 [JP] Japan ................................ 4-065525

[51] Int. Cl.$^6$ .................. C08G 18/28; C07D 327/04
[52] U.S. Cl. ..................... 528/73; 528/76; 528/293; 549/13; 549/14; 549/22; 549/30; 549/39; 549/66; 549/78
[58] Field of Search ................. 549/13, 14, 22, 549/66, 30, 39, 78; 528/73, 76, 293

[56] References Cited

U.S. PATENT DOCUMENTS

| | | |
|---|---|---|
| 4,689,387 | 8/1987 | Kajimoto et al. . |
| 4,780,522 | 10/1988 | Fajimoto et al. . |
| 5,013,496 | 5/1991 | Nagata et al. . |
| 5,021,503 | 6/1991 | Nagata et al. . |
| 5,084,545 | 1/1992 | Nagata et al. . |
| 5,087,758 | 2/1992 | Kanemura et al. . |
| 5,126,388 | 6/1992 | Nagata et al. . |

FOREIGN PATENT DOCUMENTS

| | | |
|---|---|---|
| 0329388 | 8/1989 | European Pat. Off. . |
| 0378895 | 7/1990 | European Pat. Off. . |
| 0435306 | 7/1991 | European Pat. Off. . |
| 59-87126 | 5/1984 | Japan . |
| 63-150324 | 6/1988 | Japan . |
| 63-199210 | 8/1988 | Japan . |
| 1-163701 | 6/1989 | Japan . |
| 1-242612 | 9/1989 | Japan . |
| 2-36216 | 2/1990 | Japan . |

OTHER PUBLICATIONS

Patent Abstracts of Japan, vol. 13, No. 579 (C–668) 1989; abstract of JP-A-12 042 612.
Patent Abstracts of Japan, vol. 13, No. 430 (P–937) 1989; abstract of JP-A-11 063 701.
Patent Abstracts of Japan, vol. 12, No. 482 (C–553) 1988; abstract of JP-A-63 199 210.
Patent Abstracts of Japan, vol. 12, No. 410 (C–540) 1988; abstract of JP-A-63 150 324.
Patent Abstracts of Japan, vol. 8, No. 197 (M–324) 1984; abstract of JP-A-59 087 126.

*Primary Examiner*—George F. Lesmes
*Assistant Examiner*—Helen F. Lee
*Attorney, Agent, or Firm*—Frishauf, Holtz, Goodman, Langer & Chick

[57] ABSTRACT

The present invention provides a cyclic sulfide compound represented by a general formula (I)

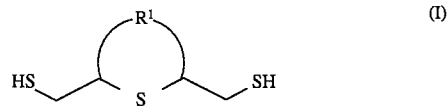

(where $R^1$ represents $-CH_2-CH_2-$, $-CH_2-CH_2-CH_2-$, $-CH_2-O-CH_2-$, $-CH_2-O-$, or $-CH_2-S-$). According to this invention, a novel cyclic sulfide compound which gives high refractive index and high Abbe number can be obtained. The polymerizable compositions for manufacturing optical products with this compound as their main component can be readily molded into plastic lenses which give superhigh refractive indices and high Abbe numbers or those which give high refractive indices and high Abbe number with low sp.grs. in addition thereto. The castings obtained from said polymerizable compositions are useful as plastic lenses for glasses, manifesting optical uniformity and being excellent in processability, transparency, and thermal, impact and light resistance. Further these polymerizable resin compositions are usable preferably as such optical products as prisms, optical fibers, optical disc substrates, color filters, or infrared absorption filters.

16 Claims, No Drawings

CYCLIC SULFIDE COMPOUND, POLYMERIZABLE COMPOSITIONS FOR OPTICAL PRODUCTS AND OPTICAL PRODUCTS FORMED THEREOF

This is a division of application Ser. No. 08/035,598 filed Mar. 23, 1993, now U.S. Pat. No. 5,446,173.

BACKGROUND OF THE INVENTION

1. Field of the Invention

The present invention relates to a novel cyclic sulfide compound, polymerizable compositions comprising it for manufacturing optical products and optical products obtained therefrom.

2. Description of the Prior Art

Plastic lenses, as compared with glass lenses, have various advantages such as light in weight, hard to crack, easy to mold and ready to dye and so on. These characteristic features being appreciated, they have recently established an important position as optical materials.

Heretofore, what is generally used as resins for lenses of eyeglass, prisms or optical fibers etc. are poly(methyl methacrylate), polycarbonate, poly(diethylene glycol bisallycarbonate) etc. Particularly, as lens materials for glasses, poly(diethylene glycol bisallylcarbonate) has most frequently been used because of its excellent transparency, processability, surface hardness and so on.

But because of its low refractive index ($n_D$= 1.50), lenses made from it for the correction of acute myopia or hypermetropia should be thick and heavy, thus raising problems that a plastic lens' advantage of being light in weight is lost and also aesthetic appearance is greatly impaired. For improving the above drawbacks, some lens materials having higher refractive indices have been proposed. Examples of compounds having refractive indices of 1.60 or higher abound, especially among compounds containing sulfur atoms (e.g. Japanese Patent Laid-Open Publication Sho 59-87126, U.S. Pat. Nos. 4,689,387 and 4,780,522, Japanese Patent Laid-Open Publication Sho 63-150324 and 63-199210, Hei 1-163701 and 1-242612, U.S. Pat. No. 5,087,758 and E.P. No. 435306).

On the other hand, the market of plastic lenses has developed along the course of nearly stepwise advances by 0.05 in the refractive index, namely from the low index of 1.50 through the middle index of 1.55–1.56 and the high index of 1.60–1.61 to the superhigh index of 1.65 or above, so that lens materials of the intermediate refractive indices (e.g. 1.58) are not much demanded. Optical products obtained by using the novel cyclic sulfide compound of this invention are those classified as products which have high or superhigh refractive indices. An important factor to be considered with materials of high refractive indices is the Abbe number, which is the index of chromatic dispersion. Generally, plastic lenses tend to have lower Abbe numbers with increasing refractive indices. Thus the chromatic dispersion becomes larger, tending to produce a rainbow at the rim of each lens, and this causes greater fatigue of the eyes. Accordingly, it is important to balance the refractive index with the Abbe number in developing commercially useful lens materials. Thus lens materials having high refractive indices and adequately high Abbe numbers are sought. Besides the refractive index and the Abbe number, important physical properties that are demanded of plastic lenses are e.g. low sp.gr. for obtaining lighter products, high thermal resistance not to be deformed by the heat of dyeing or grinding, high impact resistance to be less crackable and for assurance of higher safety, and high light resistance to avoid yellowing by ultraviolet ray etc. Balances between all of these physical properties is of importance. Lens materials hitherto proposed including those of the aforementioned prior art involved problems such that when they were designed to have higher refractive indices, 1.60 or higher, they tended to give lower Abbe numbers, increase in the sp.gr. or manifested degradation in their thermal, impact and light resistance or dyeability.

The compound disclosed in E.P. No. 435306, having an alicyclic structure with sulfide bonds, gives the lens with refractive index of the superhigh class and relatively high Abbe number. However, its addition polymerization with alicyclic polyisocyanates yielded lenses with refractive indices of 1.62 which does not meet the market's demand. Further blending with such as aliphatic polythiol as pentaerythritol tetrakis(mercaptoacetate) made it possible to adjust the refractive index to 1.60 (with the Abbe number of 40), but deterioration of the thermal resistance was notable.

SUMMARY OF THE INVENTION

The present inventors as a result of their assiduous investigations determined that the cyclic sulfide compound represented by the undermentioned general formula (I) has high refractive index and also high Abbe number, that polymerizable compositions with said compound as their principal component are excellent in processability, and moldability, that optical products obtained from said polymerizable compositions not only have either superhigh refractive indices and high Abbe numbers or low sp.grs. in addition to high refractive indices and high Abbe numbers, but are also excellent in optical uniformity, processability, and thermal, impact and light resistance, and that they are particularly quite suitable as plastic lenses for use as glasses.

Thus the present invention provides a cyclic sulfide compounds (A) represented by the undermentioned formula:

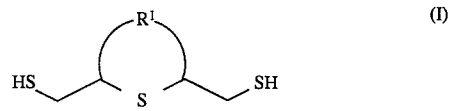
(I)

(where $R^1$ represents —$CH_2$—$CH_2$—, —$CH_2$—$CH_2$—$CH_2$—, —$CH_2$—O—$CH_2$—, —$CH_2$—O—, or —$CH_2$—S—).

The present invention also provides a polymerizable composition for manufacturing optical products comprising the aforementioned compound (A) and a compound (B) represented by a general formula (II):

(II)

(where $X^1$ and $X^2$ may be mutually identical or different and represent —N=C=O, —N=C=S,

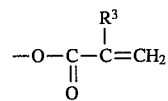

($R^3$ denotes —H or —$CH_3$), or

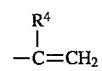

($R^4$ denotes —H or —$CH_3$); $n^1$ and $n^2$ may be identical or different and represent integers of 1–5; $R^2$ designates an organic residue with number of carbon atoms 2–25, respectively), and further provides a polymerizable composition for optical products comprising the compounds (A), (B), and a compound (C) represented by a general formula (III):

$$(Y^1)_{m_1}-R^5-(Y^2)_{m_2} \quad \text{(III)}$$

(where $Y^1$ and $Y^2$ may be mutually identical or different and denote —SH or —OH; $m^1$ and $m^2$ may be mutually identical or different and designate integers of 1–5; and $R^5$ designates an organic residue with number of carbon atoms 2–25, respectively) (however the compound (c) excludes the compound (A)) and still further provides optical products formed of copolymers of these compositions.

Throughout this Specification, iso(thio) cyanato group refers to isocyanate group and isothiocyanate group; (meth)acryloyloxy group, acryloyloxy group and methacryloyloxy group; and iso(thio)cyanate, isocyanate and isothiocyanate; and (meth)acrylate, acrylate and methacrylate.

Representative examples of the compound (A) include 2,5-bis(mercaptomethyl) tetrahydrothiophene, 2,6-bis(mercaptomethyl) tetrahydrothiopyran, 3,5-bis(mercaptomethyl)-1,4-oxathiane, 2,4-bis(mercaptomethyl)-1,3-oxathiolane and 2,4-bis(mercaptomethyl)-1,3-dithiolane.

DETAILED DESCRIPTION OF THE INVENTION

The compound (A) represented by a general formula (I) is synthesized in accordance with the reaction scheme (1) or (2) through compounds represented by the general formulae shown in the reaction scheme, which are designated by (IV), (V), (VI), (VII), (IX) and (XI) (hereinafter respectively referred to as compounds (IV), (V), (VI), (VII), (IX) and (XI)):

Reaction scheme (1):

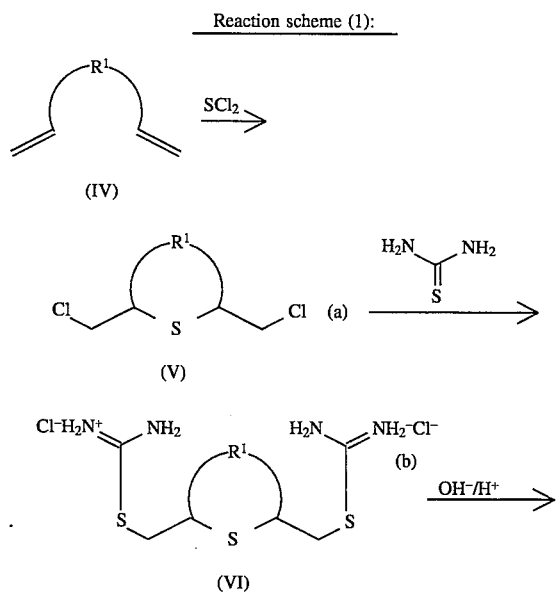

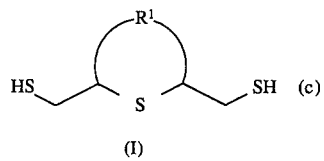

-continued
Reaction scheme (1):

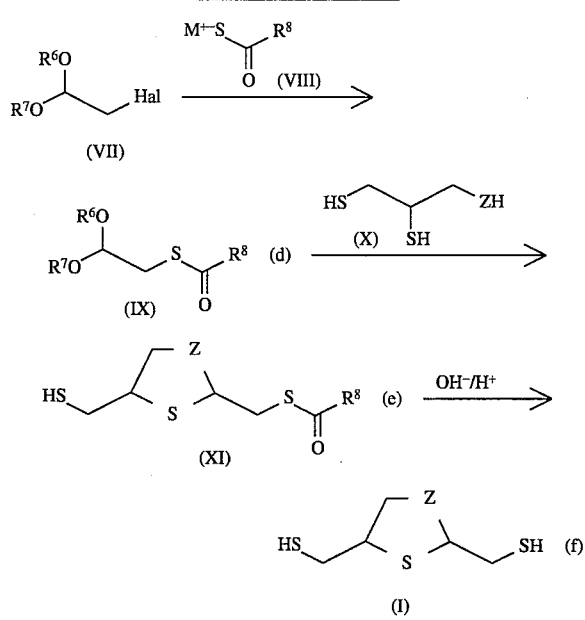

(where $R^1$ represents —$CH_2$—$CH_2$—, —$CH_2$—$CH_2$—$CH_2$—, —$CH_2$—O—$CH_2$—, —$CH_2$—O—, or —$CH_2$—S—).

(where $R^6$, $R^7$, and $R^8$ designate alkyl, aryl or aralkyl group; Hal, halogen atoms; M, alkali or alkali earth metal atoms; and Z, oxygen or sulfur atom, respectively).

In the following, the respective reactions are described in detail.

The reaction (a) is to form a compound (V) by the reaction of sulfur dichloride with a compound (IV), which includes 1,5-hexadiene, 1,6-heptadiene, allyl vinyl sulfide, allyl vinyl ether, and diallyl ether. The solvent used for this reaction should preferably be hydrocarbons (e.g. pentane, hexane, benzene, toluene, etc.), halogenated hydrocarbons (e.g. dichloromethane, 1,2-dichloroethane, etc.), ethers (e.g. diethyl ether, tetrahydrofuran, etc.), and esters (e.g. ethyl acetate, etc.).

The amount of sulfur dichloride used should be 0.5–1.5 mol, preferably 0.7–1.2 mol, per 1 mol of the compound (IV). The reaction temperature of this reaction should preferably be –30° to 50° C. and more preferably –20° C. to 30° C. At below –30° C., the reaction proceeds very slowly, but at over 50° C., by-products notably increase. It takes normally 5–50 hr for completion of this reaction.

The reaction (b) is to form a compound (VI), an isothiuronium salt, by reacting the compound (V) and thiourea. The solvent used for this reaction should preferably be alcohols (e.g. methanol, ethanol, etc.), water or aqueous alcohol. Normally, the reaction solution is heated under reflux. The amount of thiourea used should be 2 mols or more, preferably 2.0–2.4 mols, per 1 mol of the compound (V). It takes normally 1–20 hr for completion of the reaction.

The reaction (c) is to form the compound (A) represented by the general formula (I) through hydrolysis of the compound (VI) with alkali. The reaction solvent used should preferably be alcohols (e.g. methanol, ethanol, etc.), water or aqueous alcohol. The metal element used as alkali for this reaction should preferably be alkali or alkaline earth metal. Examples of preferable alkali include hydroxides (e.g. sodium hydroxide etc.), oxides (e.g. calcium oxide etc.), hydrides (e.g. sodium hydride etc.) and alkoxides (e.g. sodium methoxide etc.) of these metals. Particularly, sodium hydroxide and potassium hydroxide, which are highly reactive and low priced, are preferable. The amount of alkali used should be 2 mols or more, preferably 2.0–2.4 mols, per 1 mol of the compound (VI). The reaction temperature should preferably be 50°–100° C., at which the reaction is normally completed in 1–20 hr. After completing the reaction, the reaction solution is neutralized by adding acid, thereby liberating the compound (A). The acid used should preferably be mineral acid (e.g. hyrochloric acid, sulfuric acid, etc.) or organic acid (e.g. formic acid, acetic acid, etc.). The acid should be added until the pH of the reaction solution becomes 4–8, preferably 5–7.

The reaction (d) is to form a compound (IX) by reacting compound (VII) react with thiocarboxylate (VIII). Examples of compound (VII) include chloroacetaldehyde dimethylacetal, bromoacetaldehyde diethylacetal etc. Examples of thiocarboxylate (VIII) include potassium thioacetate, sodium thiobenzoate etc., the amount of which should be 1.0 mol or more, preferably 1.0–2.0 mols per 1 mol of compound (VII). The solvent for this reaction should preferably be alcohols (e.g. methanol, ethanol, etc.), water or amides (e.g. N,N-dimethyl formamide, etc.). The reaction temperature should preferably be 40°–100° C. Temperatures of over 100° C. are not desirable, because notable side reactions take place at such high temperatures. It takes normally 1–20 hr for completion of the reaction.

The reaction (e) is to form a compound (XI) by reacting propanedithiol derivative (X) with the compound (IX). The propanedithiol derivative (X) used should be 2,3-dimercapto-1-propanol or 1,2,3-trimercaptopropane, the amount of which should be 1.0 mol or more, preferably 1.0–2.0 mols, per 1.0 mol of the compound (IX). Because this reaction is very slow without any catalyst, addition of some acid catalyst is desirable. The acid catalyst used should preferably be Lewis acids (e.g. boron trifluoride, aluminum chloride, etc.) or mineral acid (e.g. hydrochloric acid, sulfuric acid, etc.). The amount of the catalyst should preferably be 1.0 mol or less, more preferably 0.05–0.5 mol, per 1 mol of the compound (IX). The solvent used for this reaction should preferably be hydrocarbons (e.g. hexane, toluene, etc.) or halogenated hydrocarbons (e.g. dichloromethane, 1,2-dichloroethane, etc.). It takes normally 0.5–30 hr for completion of the reaction.

The reaction (f) is to form the compound (A) represented by the general formula (I) through hydrolysis of compound (XI) with alkali under the similar conditions as in the reaction (C). However, this reaction proceeds more smoothly than the reaction (C), the reaction temperature should preferably be 0°–70° C. and a reaction time of 0.5–5 hr is sufficient.

It should be noted that when treating the compound (A) under basic condition in the reactions (c) and (f), the reactions should be run in a current of inert gas such as nitrogen, argon etc. for suppressing formation of disulfide by oxidation. The compound (A) thus obtained can be isolated in high purity through such usual refining means as solvent extraction, chromatography or distillation and so forth.

The compound (B), another component of the optical resin of this invention, is the compound having in its molecule two or more functional groups of at least one kind of the following, which react with the mercapto groups in compound (A), i.e. functional groups selected from a group consisting of iso(thio)cyanato, (meth)acryloyloxy and vinyl groups. Such compound (B) may be used singly or in mixture, but they should preferably be selected so as to provide castings having high refractive indices of 1.60–1.61 or superhigh refractive indices of 1.65 or higher to meet the demand in the market of plastic lenses. In general, with the compound (B) having aromatic rings, castings which give superhigh refractive indices of 1.65 or higher may be obtained, while aliphatic or alicyclic type of compound (B), castings which give high refractive indices of 1.60–1.61 may be obtained. One of the prominent features of the compound of this invention lies in that by merely varying the type of the compound (B), the refractive index of the resulting castings may be adjusted to high (i.e. 1.60–1.61) or to superhigh (i.e. 1.65 or higher) indices. This is quite advantageous in view of the inevitable reduction of thermal resistance of the castings using the compound of E.P. No. 435306 due to the existence of aliphatic polythiol which is added for adjustment of its refractive index.

The compound (C), another component which can be used together with the compounds (A) and (B) in the optical resins of this invention is a compound having in its molecule two or more mercapto and/or hydroxyl groups in total. Since the hydroxyl group among them reacts neither with (meth)acryloyloxy nor vinyl group, no compounds having hydroxyl groups only can be used as the compound (C), if the polymerizable functional groups of the compound (B) are (meth)acryloyloxy and/or vinyl groups only.

Actual examples of the preferable compound (B) are listed as follows: Compounds having two or more iso(thio)cyanato groups in their molecule include 1,6-hexamethylene diiso(thio)cyanate, 2,2,4- or 2,4,4-trimethylhexamethylene diiso(thio)cyanate, m-phenylene diiso(thio)cyanate, 2,4- or 2,6-tolyelene diiso(thio)cyanate, m-xylylene diiso(thio)cyanate, α,α'-dimethylxylylene diiso(thio)cyanate, α,α,α',α'-tetramethyl xylylene diiso(thio)cyanate, 4,4'-diphenylmethane diiso(thio)cyanate, 4,4'-diiso(thio)cyanato-3,3'-dimethylbiphenyl, 4,4'-diiso(thio)cyanato-3,3'-dimethyl diphenylmethane, 1,5-naphthylene diiso(thio)cyanate, 1,3,5-benzene triiso(thio)cyanate, 4,4',4"-triiso(thio)cyanatotriphenymethane, isophorone diiso(thio)cyanate, 1,3-bis(iso(thio)cyanatomethyl) cyclohexane, 1,3,5-tri(iso(thio)cyanatomethyl) cyclohexane, 4,4'-dicyclohexylemthane diiso(thio)cyanate, 2,5-bis(iso(thio)cyanatomethyl)bicyclo[2.2.1]heptane, 3,8-bis(iso(thio)cyanatomethyl)tricyclo[5.2.1.0$^{2,6}$] decane, etc.

Examples of compound (B) having in their molecule two or more (meth)acryloyloxy or vinyl groups include ethylene glycol di(meth)acrylate, 1,4-butanediol di(meth)acrylate, trimethylolpropane tri(meth)acrylate, pentaerythritol tetra(meth)acrylate, 1,3- or 1,4-cyclohexanediol di(meth)acrylate, 1,4-cyclohexane dimethanol di(meth)acrylate, p-xylylene glycol di(meth)acrylate, bisphenol-A di(meth)acrylate, divinyl benzene, o-bis(vinylsulfonylmethyl)benzene, etc.

Examples of compound (B) having in their molecule one or more iso(thio)cyanato group(s) and one or more (meth)acryloyloxy or vinyl group(s) include 2-iso(thio)cyanatoethyl (meth)acrylate, 3- or 4-vinylbenzyl iso(thio)cyanate, 3- or 4-vinyl-α,α-dimethylbenzyl iso(thio)cyanate, 3- or 4-isopropenyl-α,α-dimethylbenzyl iso(thio)cyanate etc.

Examples of the compound (C) used according to this invention include 1,2-ethanedithio, 1,2- or 1,3-propanedithiol, 1,4-butanedithiol, 1,6-hexanedithiol, 1,10-decanedithiol, bis(2-mercaptoethyl)ether, 1,2-bis-(2'-mercaptoethyloxy)ethane, bis(2-mercaptoethyl)sulfide, 1,2-benzenedithiol, 3,4-toluenedithiol, 4,5-bis(mercaptomethyl)-o-xylylene, 1,3,5-benzenetrithiol, m- or p-xylylenedithiol, 1,3,5-tris(mercaptomethyl)benzene, 4,4'-dimercaptobiphenyl, 3,3'-dimethyl-4,4'-dimercaptobiphenyl, ethylene glycol bis(mercaptoacetate), 1,4-butanediol bis(mercaptoacetate), trimethylolpropane tris(mercaptoacetate), pentaerythritol tetrakis(mercaptoacetate), trimethylolpropane tris($\beta$-meraptopropionate), pentaerythritol tetrakis($\beta$-mercaptopropionate), 2-mercaptoethanol, 2-mercapto-1-propanol, 3-mercapto-1,2-propanediol, 2,3-dimercapto-1-propanol, 1,2,3-trimercaptopropane, dithioerythritol, 2-mercapto-4-merthyl-5-($\beta$-hydroxyethyl)thiazoline, p-mercaptophenol, 2,2'-thiodiethanol, 2,2'-dithiodiethanol, tetramethylene bis($\beta$-hydroxyethylsulfide), 4,4'-thiodiphenol, ethylene glycol, 1,2-propylene glycol, 1,4 butanediol, 1,6-hexanediol, diethylene glycol, triethylene glycol, p-xylylene glycol, glyercine etc.

With regard to the amounts of compounds (A), (B) and (C) used in the optical resins of this invention, when the compound (B) has iso(thio)cyanato group(s) as the polymerizable functional groups, the total mol number of iso(thio)cyanato, (meth)acryloyloxy and vinyl groups in the compound (B) should be 1–3 times, preferably 1–1.5 times, of the total mol number of mercapto groups in the compound (A) or the total mol number of mercapto groups in the compound (A) and mercapto and/or hyroxyl groups in the compound (C). When compound (B) has (meth)acryloyloxy and vinyl groups only, the total mol number of (meth)acryloyloxy and vinyl groups in the compound (B) should be 1–3 times, preferably 1–1.5 times, of the total mol number of mercapto groups in the compound (A) or mixtures of compounds (A) and (C). The amount of the compound (C) used should be the same or less, preferably 0.5 times or less, of the mol number of the compound (A). If the amount of compound (C) falls out of this range, the characteristic features of high refractive indices and high Abbe numbers that the optical resins of this invention have will be lost.

When optical resins are molded by copolymerizing mixtures of the aforementioned compounds (A) and (B) or mixtures of the compounds (A), (B) and (C), sometimes some catalysts are added for adjusting the rate of polymerization. Particularly when copolymerization is performed with the compound (B) having (meth)acryloyloxy or vinyl group(s) without addition of any catalyst, the rate of addition of the mercapto group to the double bond is very slow. The suitable catalysts with compound (B) having two or more iso(thio)cyanato groups, which accelerate the reaction of iso(thio)cyanato group with mercapto or hydroxyl group, are organic tin compounds (e.g. dibutyltin dilaurate, tin di(2-ethylhexoate), dibuytyltin dichloride etc.) and aliphatic tertiary amines (e.g. N,N,N',N'-tetramethylethylenediamine, 1,4-diazabicyclo-[2.2.2]octane etc.). The suitable catalysts with compound (B) having (meth)acryloyloxy or vinyl group(s) are those which are generally used in radical polymerization reaction. Actual examples include peroxides (e.g. benzoyl peroxide, diisopropyl peroxydicarbonate etc.) and azo compounds (e.g. azobis(isobutyronitrile), azobis(2, 4-dimethylvaleronitrile) etc.). When compound (B) has one or more iso(thio)cyanato group(s) and one or more (meth)acryloyloxy group(s) or vinyl group(s), joint use of the aforementioned two types of catalysts is preferable. The amount of such catalyst(s) is not particularly limited, but normally 0.01–10 per hundred resin (hereinafter abbreviated to PHR based on weight). For satisfying the demands for various properties or performances of the lens, small amounts of stabilizers, ultraviolet adsorbents, antioxidants, coloring agents, internal demolding agents and so on may be added to the optical resins of this invention as required.

Polymerization of the resins of this invention may be carried out by the hitherto-known casting polymerization method. For example, compounds (B) and (A) or these compounds with addition of the compound (C) are mixed, some catalyst(s) and/or various additives are added, if necessary, and the mixture is degassed under reduced pressure; thereafter the mixture is poured into a pair of glass or metal mold with resin gasket and the polymerization is completed by gradually raising the temperature. The temperature range of the polymerization is not limited, but normally its range is −50° to 150° C. The duration of polymerization is normally 0.5–72 hr, preferably 20–40 hr, depending on the manner of polymerization and the heat of polymerization.

The compound (A) of this invention gives high refractive index and high Abbe number, because it has in its molecule two mercapto groups and one or two sulfide groups, which are bonded not by an aromatic ring(s) but by an aliphatic carbon chain(s). Because the compound (A) has relatively small vapor pressure, the stink peculiar to mercapto compounds is appreciably slight. Therefore the workability in the manufacture of the resins and plastic lenses comprising this compound (A) is quite good. In addition, the compound (A), having 5- or 6-membered ring cyclic structure, is thermally stable which is easily refinable by distillation. The copolymers of compounds (A) and (B) or the copolymers of compounds (A), (B) and (C) not only have the compound (A)'s characteristic features of high refractive index and high Abbe number, but have such excellent characteristic features as being transparent and optically uniform. The compound (A) may be molded into plastic lenses with superhigh or high refractive indices merely by altering the type of the compound (B). This leads to a great advantage that mixing-in of large quantity of other components otherwise required for adjusting the refractive index of the casting is circumvented for the benefit of preservation of the excellent physical properties peculiar to these products. They are excellent also in thermal, impact and light resistance.

EXAMPLES

This invention is illustrated by the following Examples, but should not be construed to be limited thereto.

In the following Examples, various physical properties of the compound of this invention and the polymers derived therefrom were measured by the undermentioned methods:
(1) Mass spectrometry (MS)

MS was measured with mass spectrometer "AX-505W" of Nihon Denshi Co. Ltd. The sample was introduced by direct introduction (DI) method, then ionized by electron ionization (EI) method.
(2) Nuclear magnetic resonance spectroscopy ($^1$H-NMR)

$^1$H-NMR spectrum was measured with FT-NMR spectrometer "GSX-270" (270 MH$_z$) of Nihon Denshi Co. Ltd., with chloroform-d as the solvent and tetramethylsilane as the internal standard.
(3) Refractive index ($n_D$) and Abbe number ($v_D$)

A test piece of 10×20×3 mm of the casting or a liquid film of compound (A) was prepared. Its index of refraction ($n_D$) and Abbe number ($v_D$) at 30° C. were measured using Abbe refractometer "3T" of Atago Co. Ltd. As the contacting liquid, diiodomethane was used.
(4) Sp.gr. (d)

Using a test piece of 10×20×3 mm, the sp.gr. was measured with "DENSIMETER D-1" of Toyo Seiki Seisakusho Co. Ltd.

(5) Yellow index (b*)

Using a test piece of 30×30×3 mm, yellow index was measured with calorimeter "CR-300" of Minolta Camera Co., Ltd. The value represents the yellow index (b*) of L*a*b* system of CIE (Commission Internationale de l'Eclairage, Paris, 1976).

It is desired that the yellow index is closer to zero. Practically less than 1.0 is preferable.

(6) Thermal resistance

1) Thermomechanical analysis (TMA)

TMA measurement was performed by using "TMA 120C" of Seiko Denshi Co. Ltd., with a load of 10 gf applied on a 7×7×3 mm test piece of the casting and while raising the temperature at a rate of 2.0° C./min. The softening point was read from the point of inflection in the TMA curve.

2) Vicat softening temperature (VST)

VST measurement was performed by using "HDT & VSPT TESTER" of Toyo Seiki Seisakusho Co., Ltd., with a load of 1.0 kgf applied on a 10×10×3 mm test piece of the casting in silicone oil, while raising the temperature at a rate of 50° C./hr. The temperature when a needle-shaped penetrator has penetrated into the test piece of 0.1 mm was measured.

(7) Impact resistance

Ten test sheets with 78 mm dia., 0.1 m radius of curvature and 1.3 mm central thickness were prepared. A steel ball weighing 16.2 g ($^{10}/_{16}$ inch dia.) was dropped on the test sample from a level of 1.27 m (50 inch). The outcome is shown as "good", when all ten sheets were not broken, but "poor", if any one sheet was broken.

(8) Light resistance

A casting of 30×30×2 mm was irradiated for 1 month with a JAS (Japanese Agricultural Standard) specified faeometer (with a 1 mW/cm² UV intensity, and irradiation wave length 320–390 nm). The yellowness of the test sample was measured with calorimeter "CR-300" of Minolta Camera Co. Ltd. When the value of yellowness (b*) of the test sample was not more than twice the initial value, it was scored as "good", and when larger than twice, it was scored as "poor".

EXAMPLE 1

A 50 ml pentane solution of 35.2 g of 1,5-hexadiene and a 25 ml pentane solution of 36.9 g of sulfur dichloride were concurrently added dropwise into 625 ml of pentane at the room temperature in 1 hr in such a way that equimolar amount of each substrate is added and the mixture was stirred at room temperature for further 12 hr. The polymeric material which had precipitated was removed by decantation and filtration and pentane was removed under reduced pressure. The residue was distilled under reduced pressure, and a fraction with a b.p. of 102° C./3.5 torr was collected to yield 45.5 g of 2,5-bis(chloromethyl) tetrahydrothiophene. Yield 68.6%.

Next, to a 200 ml ethanol solution of 37.4 g of the above compound was added 32.8 g of thiourea and heated for 6 hr under reflux. The precipitate was filtered off, washed with ethanol, and dried to yield 55.7 g of isothiuronium salt. Yield 81.8%.

Subsequently, 55.7 g of this salt was added to a 200 ml aqueous solution of 15.1 g of sodium hydroxide. The solution was heated at 80° C. for 4 hr, then neutralized to pH 6 with 35% hydrochloric acid. The product was extracted with dichloromethane and the extract was dried over anhydrous magnesium sulfate, followed by filtration. Dichloromethane was removed under reduced pressure. The residue was distilled under reduced pressure and a fraction with a b.p. of 126° C./3.5 torr was collected to yield 25.4 g of 2,5-bis(mercaptomethyl) tetrahydrothiophene. Yield 85.2%.

$n_D$=1.602

$v_D$=36.7

MS:m/z=180 (M⁺)

¹H-HMR:δ(ppm)

1.63 (2H, s, —S$\underline{H}$)

1.91–1.98, 2.10–2.16 (4H, m, —(C$\underline{H}_2$)₂—)

2.72 (4H, d, —C$\underline{H}_2$SH)

3.52–3.57 (2H, m, >C$\underline{H}$S—)

EXAMPLE 2

A 25 ml dichloromethane solution of 33.0 g of sulfur dichloride was added dropwise into a 675 ml dichloromethane solution of 42.1 g of diallyl ether at −15 C. in 1 hr and subsequently the mixture was stirred at 0 C. for further 12 hr. Dichloromethane was removed under reduced pressure. The residue was distilled under reduced pressure, and a fraction with a b.p. of 100° C./1 torr was collected to yield 31.8 g of 3,5-bis(chloromethyl)-1,4-oxathiane. Yield 49.3%.

Next, 29.8 g of this compound and 25.3 g of thiourea were heated for 7 hr in 200 ml of ethanol under reflux. The precipitate was filtered off and washed with ethanol, followed by drying to yield 40.5 g of isothiuronium salt. Yield 77.3%.

Subsequently, 40.5 g of this salt was added to a 200 ml aqueous solution of 13.1 g of sodium hydroxide. This solution was heated at 80° C. for 4 hr, and neutralized to pH 6 with 35% hydrochloric acid. The product was extracted with dichloromethane. The extract was dried with over anhydrous magnesium sulfate, filtered, and dichloromethane was removed under reduced pressure. The residue was distilled under reduced pressure and a fraction with a b.p. of 131° C./1.5 torr was then collected, yielding 18.3 g of 3,5-bis(mercaptomethyl)-1,4-oxathiane. Yield 81.4%.

$n_D$=1.597

$v_D$=37.9

MS:m/z=196 (M⁺)

¹H-HMR:δ(ppm)

1.64 (2H, t, J=8.40 Hz, —S$\underline{H}$)

2.65 (4H, dt, J=8.40, 1.80 Hz, —(C$\underline{H}_2$)SH)

2.98–3.08 (2H, m, >C$\underline{H}$S—)

3.43 (2H, dd, J=11.60, 8.85 Hz —$\underline{H}$CHO—)

4.23 (2H, dd, J=11.60, 3.34 Hz —HC$\underline{H}$O—)

EXAMPLE 3

A 15 ml ethanol solution of 11.5 g of thioacetic acid was added dropwise to a 170 ml ethanol solution of 8.5 g of granular potassium hydroxide and subsequently a 15 ml ethanol solution of 20.1 g of bromoacetaldehyde diethyl acetal was added dropwise. The mixture was then heated for 12 hr under reflux. Ethanol was distilled off under reduced pressure, water was added and the oily substance separated was extracted with ethyl acetate. The extract was dried over anhydrous magnesium sulfate, filtered, and ethyl acetate was removed under reduced pressure. The residue was then distilled under reduced pressure and a fraction with a b.p. of 125° C./33 torr was collected to yield 16.3 g of acetylthio-acetaldehyde diethyl acetal. Yield 78.8%.

Next, into a 60 ml dichloromethane solution of 9.9 g of this compound were added 7.5 g of 1,2,3-trimercaptopropane and 4 ml of boron trifluoride etherate at room temperature and the mixture was then stirred for 1 hr. The solution was washed with water and dried over anhydrous magnesium sulfate, filtered, and dichloromethane was then removed under reduced pressure. Subsequently, 100 ml of methanol and 6.5 g of sodium hydroxide were added to the residue and the mixture was stirred at room temperature for 30 min. After neutralizing the solution with dilute hydrochloric acid, the product was extracted with dichloromethane and the extract was dried over anhydrous magnesium sulfate, and filtered. Dichloromethane was removed under reduced pressure. The residue was then distilled under reduced pressure and a fraction with a b.p. of 134°–138° C./0.5 torr was collected to yield 6.7 g of 2,4-bis(mercaptomethyl)-1,3-dithiolane. Yield 65.0%.

$n_D$=1.648

$v_D$=35.0

MS:m/z=198 (M$^+$)

$^1$H-HMR:δ(ppm)

1.64, 1.70 (1H(total), t(each), J=8.55 Hz, —S$\underline{H}$)

1.89, 1.90 (1H(total), t(each), J=8.55 Hz, —S$\underline{H}$)

2.76–2.92 (4H, m, —C$\underline{H_2}$SH)

3.20–3.38 (2H, m, —SC$\underline{H_2}$S—)

3.83–3.88 (1H, m, —SC$\underline{H}$CH$_2$S—)

4.56, 4.63 (1H(total), t(each), J=7.02 Hz, —SC$\underline{H}$S—)

EXAMPLE 4

1.82 g of 2,5-bis(mercaptomethyl) tetrahydrothiophene obtained in Example 1 and 2.00 g of 1,3-bis(isocyanatomethyl)cyclohexane were mixed. The mixture was homogenized with 5.4 mg (0.14 PHR) of dibutyl tin dilaurate added as a polymerization catalyst, further well degassed under reduced pressure, thereafter put into a glass mold with gasket and polymerized by heating in an air oven. The temperature of the oven was raised from 40° C. to 60° C. in 10 hr, holding the system at 60° C. for 4 hr, again raising the temperature from 60° C. to 120° C. in 1 hr, holding it at 120° C. for 3 hr and cooling from 120° C. to 60° C. in 2 hr. The physical properties of the casting obtained in this way was summarized in Table 1. They clearly indicate that this casting shows a high refractive index and a high Abbe number and is excellent in transparency and thermal, impact and light resistance.

EXAMPLES 5–15

The cyclic sulfide compound (A) manufactured by the methods of Examples 1–3 and the compound (B) (and compound (C)) shown in Tables 1 were mixed. Then these mixtures were cast under the conditions similar to those of Example 4, after adding optional polymerization catalyst shown in Table 1. The physical properties of the castings obtained in this way are shown in Table 1. These castings all gave high or superhigh refractive indices and high Abbe numbers, which are well balanced, and were colorless and excellent in transparency and thermal, impact and light resistance.

Comparative Examples 1–5

The polymerizable compositions with optional polymerization catalyst given in Table 2 were casted under conditions similar to those of Example 4, and the properties of the products are shown in Table 2. These castings were unsatisfactory either in the refractive index, the Abbe number, yellow index, thermal, impact or light resistance, thus being clearly inferior to the castings of this invention in the aspect of physical properties. It should be noted that the composition of Comparative Example 4 corresponds to the composition disclosed in E.P. No. 435306.

According to this invention, a novel cyclic sulfide compound with high refractive index and high Abbe number can be obtained. Polymerizable compositions for optical products with these compounds as their main component can be readily molded into plastic lenses with superhigh refractive indices and high Abbe numbers or plastic lenses with high refractive indices, high Abbe numbers and low sp.grs. Moreover, the molds obtained from said polymerizable compositions are useful as plastic lenses for glasses, being optionally uniform and excellent in processability, transparency and thermal, impact and light resistance. Further, these polymerizable resin compositions are favorably usable for such optical products as prisms, optical fibers, optical disc substrates, color filters or infrared absorption filters etc.

TABLE 1

A = Compound (A) g (mmol)
B = Compound (B) g (mmol)
C = Compound (C) g (mmol)
D = Catalyst mg (PHR)

| Example No. | | | | | Refractive Index $n_D$ | Abbe Number $v_D$ | Specific Gravity d | Yellow Index b* | TMA /°C. | VST /°C. | Impact Resistance | Light Resistance |
|---|---|---|---|---|---|---|---|---|---|---|---|---|
| 4 | A | 2,5-Bis(mercaptomethyl) tetrahydrothiophene | 1.82 | (10.1) | 1.61 | 40 | 1.26 | 0.8 | 104 | 95 | good | good |
|   | B | 1,3-Bis(isocyanatomethyl) cyclohexane | 2.00 | (10.3) | | | | | | | | |
|   | D | Dibutyltin dilaurate | 5.4 | (0.14) | | | | | | | | |
| 5 | A | 3,5-Bis(mercaptomethyl)-1,4-oxathiane | 1.96 | (9.98) | 1.60 | 40 | 1.29 | 0.8 | 104 | 97 | good | good |
|   | B | 1,3-Bis(isocyanatomethyl) cyclohexane | 1.96 | (10.1) | | | | | | | | |
|   | D | Dibutyltin dilaurate | 5.6 | (0.14) | | | | | | | | |
| 6 | A | 2,4-Bis(mercaptomethyl)-1,3-dithiolane | 1.98 | (9.98) | 1.60 | 40 | 1.26 | 0.9 | 105 | 99 | good | good |
|   | B | 1,6-Hexamethylene diisocyanate | 1.78 | (10.6) | | | | | | | | |

TABLE 1-continued

A = Compound (A) g (mmol)
B = Compound (B) g (mmol)
C = Compound (C) g (mmol)
D = Catalyst mg (PHR)

| Example No. | | | | | Refractive Index $n_D$ | Abbe Number $v_D$ | Specific Gravity d | Yellow Index b* | TMA /°C. | VST /°C. | Impact Resistance | Light Resistance |
|---|---|---|---|---|---|---|---|---|---|---|---|---|
| | D | Dibutyltin dichloride | 5.9 | (0.16) | | | | | | | | |
| 7 | A | 2,5-Bis(mercaptomethyl) tetrahydrothiophene | 1.84 | (10.2) | 1.65 | 32 | 1.33 | 0.9 | 90 | 85 | good | good |
| | B | m-Xylylene diisocyanate | 1.90 | (10.1) | | | | | | | | |
| | D | Dibutyltin dilaurate | 5.5 | (0.15) | | | | | | | | |
| 8 | A | 3,5-Bis(mercaptomethyl)-1,4-oxathiane | 1.98 | (10.1) | 1.65 | 33 | 1.35 | 0.9 | 100 | 88 | good | good |
| | B | m-Xylylene diisocyanate | 1.90 | (10.1) | | | | | | | | |
| | D | Dibutyltin dilaurate | 5.9 | (0.15) | | | | | | | | |
| 9 | A | 2,4-Bis(mercaptomethyl)-1,3-dithiolane | 1.98 | (9.98) | 1.67 | 31 | 1.38 | 0.9 | 109 | 95 | good | good |
| | B | m-Xylylene diisocyanate | 1.93 | (10.3) | | | | | | | | |
| 10 | A | 2,5-Bis(mercaptomethyl) tetrahydrothiophene | 1.64 | (9.09) | 1.60 | 41 | 1.18 | 0.9 | 106 | 94 | good | good |
| | B | Isophorone diisocyanate | 2.33 | (10.6) | | | | | | | | |
| | C | 1,2,3-Trimercaptopropane | 0.14 | (1.0) | | | | | | | | |
| | D | Dibutyltin dichloride | 5.9 | (0.14) | | | | | | | | |
| 11 | A | 2,5-Bis(mercaptomethyl) tetrahydrothiophene | 1.83 | (10.1) | 1.62 | 38 | 1.26 | 0.8 | 114 | 108 | good | good |
| | B | m-Xylylene diisocyanate | 1.05 | (5.58) | | | | | | | | |
| | B | Trimethylolpropane trimethacrylate | 1.07 | (3.16) | | | | | | | | |
| | D | Dibutyltin dichloride | 8.8 | (0.22) | | | | | | | | |
| | D | Azobis(2,4-dimethyl valeronitrile) | 17.4 | (0.44) | | | | | | | | |
| 12 | A | 3,5-Bis(mercaptomethyl)-1,4-oxathiane | 1.78 | (9.07) | 1.60 | 35 | 1.19 | 0.8 | 92 | 87 | good | good |
| | B | m-Xylylene diisocyanate | 2.00 | (10.7) | | | | | | | | |
| | C | 3-Mercapto-1,2-propanediol | 0.12 | (1.1) | | | | | | | | |
| | D | Dibutyltin dichloride | 6.4 | (0.16) | | | | | | | | |
| 13 | A | 3,5-Bis(mercaptomethyl)-1,4-oxathiane | 1.97 | (9.99) | 1.65 | 30 | 1.37 | 0.9 | 126 | 112 | good | good |
| | B | m-Xylylene diisocyanate | 1.11 | (5.92) | | | | | | | | |
| | B | 4,4',4"-Triphenylmethane triisocyanate | 1.00 | (2.72) | | | | | | | | |
| | D | Dibutyltin dichloride | 28.0 | (0.69) | | | | | | | | |
| 14 | A | 2,4-Bis(mercaptomethyl)-1,3-dithiolane | 2.28 | (11.5) | 1.60 | 40 | 1.27 | 0.9 | 93 | 89 | good | good |
| | B | 1,3-Bis(isocyanatomethyl) cyclohexane | 1.93 | (9.94) | | | | | | | | |
| | B | 2-Isocyanatoethyl methacrylate | 0.46 | (3.0) | | | | | | | | |
| | D | Dibutyltin dilaurate | 5.7 | (0.12) | | | | | | | | |
| | D | Benzoyl peroxide | 56.7 | (1.21) | | | | | | | | |
| 15 | A | 2,4-Bis(mercaptomethyl)-1,3-dithiolane | 1.98 | (9.98) | 1.60 | 40 | 1.30 | 0.9 | 91 | 88 | good | good |
| | B | Ethylene glycol dimethacrylate | 1.98 | (9.98) | | | | | | | | |
| | D | Azobis(2,4-dimethyl valeronitrile) | 17.9 | (0.45) | | | | | | | | |

TABLE 2

P = Polymerizable component g (mmol)
D = Catalyst mg (PHR)

| Comparative Example No. | | | | | Refractive Index $n_D$ | Abbe Number $v_D$ | Specific Gravity d | Yellow Index b* | TMA /°C. | VST /°C. | Impact Resistance | Light Resistance |
|---|---|---|---|---|---|---|---|---|---|---|---|---|
| 1 | P | Diethylene glycol bisallyl carbonate | 4.54 | (16.8) | 1.50 | 58 | 1.32 | 0.9 | 93 | 85 | poor | good |

TABLE 2-continued

P = Polymerizable component g (mmol)
D = Catalyst mg (PHR)

| Comparative Example No. | | | | | Refractive Index $n_D$ | Abbe Number $v_D$ | Specific Gravity d | Yellow Index b* | TMA /°C. | VST /°C. | Impact Resistance | Light Resistance |
|---|---|---|---|---|---|---|---|---|---|---|---|---|
| | D | Diisopropylperoxy dicarbonate | 201 | (4.43) | | | | | | | | |
| 2 | P | 2,2-Bis(4-(2-methacryloyloxyethyloxy)-3,5-dibromo-phenyl)propane | 2.45 | (3.19) | 1.60 | 30 | 1.38 | 1.1 | 100 | 86 | poor | poor |
| | P | Styrene | 1.54 | (14.6) | | | | | | | | |
| | D | Azobis(2,4-dimethyl valeronitrile) | 39.6 | (0.99) | | | | | | | | |
| 3 | P | Pentaerythritol tetrakis(β-mercapto-propionate) | 2.51 | (5.13) | 1.60 | 36 | 1.36 | 1.0 | 73 | 72 | good | good |
| | P | m-Xylylene diisocyanate | 1.99 | (10.2) | | | | | | | | |
| | D | Dibutyltin dilaurate | 5.7 | (0.14) | | | | | | | | |
| 4 | P | 2,5-Bis(mercaptomethyl)-1,4-dithiane | 1.26 | (5.95) | 1.60 | 40 | 1.31 | 0.9 | 115 | 74 | good | good |
| | P | Pentaerythritol tetrakis(mercaptoacetate) | 0.85 | (2.0) | | | | | | | | |
| | P | 1,3-Bis(isocyanatomethyl) cyclohexane | 1.95 | (10.0) | | | | | | | | |
| | D | Dibutyltin dichloride | 5.3 | (0.13) | | | | | | | | |
| 5 | P | m-Xylylene dithiol | 1.94 | (11.5) | 1.66 | 28 | 1.38 | 4.1 | 77 | 72 | good | good |
| | P | m-Xylylene diisocyanate | 2.16 | (11.5) | | | | | | | | |

What is claimed is:

1. A polymerizable composition for manufacturing optical products comprising the compound (A) represented by the general formula (I)

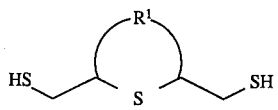

(I)

where $R^1$ represents —$CH_2$—$CH_2$—, —$CH_2$—$CH_2CH_2$—, —$CH_2O$—$CH_2$, —$CH_2$—O—, or —$CH_2$—S—;
a compound (B) represented by a general formula (II):

(II)

where $X^1$ and $X^2$ may be identical or different and represent —N=C=O, —N=C=S,

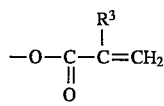

wherein $R^3$ designates —H or —$CH_3$ or

wherein $R^4$ denotes —H or —$CH_3$, $n^1$ and $n^2$ may be identical or different and represent integers of 1–5; $R^2$ designates an organic residue with number of carbon atoms 2–25, respectively and, optionally, a compound (C) represented by a general formula (III):

(III)

wherein $Y^1$ and $Y^2$ may be mutually identical or different and denote —SH or —OH, $m^1$ and $m^2$ may be mutually identical or different and designate integers of 1–5; $R^6$ designates an organic residue with number of carbon atoms 2–25, respectively, the compound (C) excluding the compound (A).

2. The polymerizable composition according to claim 1, wherein the compound (B) is any of alicyclic compounds with one or more rings, or their mixtures.

3. The polymerizable composition according to claim 2, wherein the compound (B) is any of compounds having a cyclohexane ring(s) or their mixtures.

4. The polymerizable composition according to claim 3, wherein the compound (B) is 1,3-bis(isocyanatomethyl) cyclohexane or isophorone diisocyanate.

5. The polymerizable composition according to claim 1, wherein the compound (B) is any of compounds having an aromatic ring(s) or their mixtures.

6. The polymerizable composition according to claim 5, wherein the compound (B) is m-xylylene diisocyanate, α,α,α',α'-tetramethylxylylene diisocyanate, 4,4',4"-triphenylmethane triisocyanate or 3-isopropenyl-α,α-dimethylbenzyl isocyanate.

7. The polymerizable composition according to claim 1, wherein the compound (B) is any of aliphatic compounds or their mixtures.

8. The polymerizable composition according to claim 7, wherein the compound (B) is 1,6-hexamethylene diisocyanate, 2-isocyanatoethyl methacrylate, ethylene glycol dimethacrylate or trimethylolpropane trimethacrylate.

9. The polymerizable composition according to claim 1, wherein the compound (C) is any of aliphatic compounds or their mixtures.

10. The polymerizable composition according to claim 9, wherein the compound (C) is 1,2,3-trimercaptopropane, 3-mercapto-1,2-propanediol, 2,3-dimercapto-1-propanol, glycerine, trimethylolpropane tris(mercaptoacetate), pentaerythritol tetrakis(mercaptoacetate), trimethylol propane tris(β-mercaptopropionate) or pentaerythritol tetrakis(β-mercaptopropionate).

11. The polymerizable composition according to claim 1, wherein the compound (C) is any of compounds having an aromatic ring(s) or their mixtures.

12. The polymerizable composition according to claim 11, wherein the compound (C) is m-xylylenedithiol, 1,3,5-tris(mercaptomethyl)benzene or p-xylylene glycol.

13. The polymerizable composition according to claim 1, wherein compound (A) is 2,5-bis(mercaptomethyl) tetrahydrothiophene, compound (B) is 1,3-bis(isocyanatomethyl) cyclohexane, and compound (C) is 1,2,3-trimercaptopropane.

14. The polymerizable composition for manufacturing optical products according to claim 1, and including said compound (c).

15. An optical product formed by copolymerizing the polymerizable composition of claim 1.

16. The optical product of claim 15, which is a plastic lens.

* * * * *